United States Patent [19]

Katakura et al.

[11] Patent Number: 5,484,572
[45] Date of Patent: Jan. 16, 1996

[54] APPARATUS FOR COLLECTING MEDICAL TEST SPECIMENS

[75] Inventors: Takaaki Katakura; Hidemasa Mouri, both of Yokohama; Minoru Nakamuta, Ryugasaki, all of Japan

[73] Assignee: Taiho Industries Co., Ltd., Tokyo, Japan

[21] Appl. No.: 257,187

[22] Filed: Jun. 8, 1994

[30] Foreign Application Priority Data

Oct. 1, 1993 [JP] Japan .................................. 5-267740

[51] Int. Cl.$^6$ ............................. B01L 11/00; B01L 3/00
[52] U.S. Cl. ................................... 422/101; 422/102
[58] Field of Search ............................ 422/101, 102; 436/178; 435/299, 300

[56] References Cited

U.S. PATENT DOCUMENTS

| | | | |
|---|---|---|---|
| 3,615,257 | 10/1971 | Frost | 422/101 |
| 4,696,797 | 9/1987 | Kelton | 422/101 |
| 5,219,525 | 6/1993 | Harrison | 422/58 |
| 5,234,593 | 8/1993 | Kuroki et al. | 210/426 |
| 5,252,293 | 10/1993 | Drbral et al. | 422/101 |
| 5,252,460 | 10/1993 | Fiedler et al. | 435/7.22 |
| 5,266,209 | 11/1993 | Knight et al. | 210/691 |
| 5,272,083 | 12/1993 | Butz et al. | 435/240 |
| 5,308,483 | 5/1994 | Sklar et al. | 210/232 |
| 5,330,916 | 7/1994 | Williams et al. | 435/311 |

FOREIGN PATENT DOCUMENTS 2098087 11/1982 United Kingdom .
9013802 11/1990 WIPO .

*Primary Examiner*—Robert J. Warden
*Assistant Examiner*—N. Bhat
*Attorney, Agent, or Firm*—Oblon, Spivak, McClelland, Maier & Neustadt

[57] ABSTRACT

A method for collecting medical test specimens which includes placing a sample fluid in a cup container having an outlet and pressurization mechanism to increase the internal air pressure, disposing a specimen collection film so as to provide an airtight seal of the cup container outlet, and using the pressurization mechanism to increase the air pressure in the cup so as to force the sample fluid out through the outlet and capture specimens in the sample fluid on the film.

4 Claims, 8 Drawing Sheets

APPARATUS FOR COLLECTING MEDICAL TEST SPECIMENS

BACKGROUND OF THE INVENTION

1. Field of the Invention

The present invention relates to a method and apparatus for collecting cancer or other cells present in urine and other body fluids for microscopic examination for diagnostic or therapy purposes.

2. Description of the Prior Art

Urine, saliva, sputum and uterine secretions and other such fluids for testing are forced under pressure through a filter that consists of a plastic film some 10 μm thick evenly perforated with substantially round holes about 5 μm in diameter. The liquid portion of the body fluid passes through the perforations while the object specimen cells are retained on the plastic film. Concentrated body fluids are suitably diluted before filtration.

When the cells on the film are stained and examined under the microscope, if cancer cells are found the diagnosis is that cancer is present where the fluid was secreted. The method is not limited to cancer cells, and can be effectively applied to diagnoses relating to the whole range of body fluid components. In recent years, some major hospitals that have instituted this method have reported a high rate of cancer discovery.

FIG. 12 is a side cross-sectional view of an arrangement of a conventional apparatus for obtaining medical test specimens, FIG. 13 is a perspective view of a conventional specimen collection element, and FIG. 14 is a side view of a plurality of specimen collection elements, each consisting of a lower support member and an upper support member, arranged on a suction apparatus.

In the drawings, reference numeral 1 denotes a known specimen collection element comprised of a thin, stiff plate 2 with a round hole 2a at its center, and a plastic film 3 attached on the plate 2 so that the hole 2a is covered. Reference number 4 represents a lower support member which, with an upper support member 5, provides airtight support for the specimen collection element 1. The top of the lower support member 4 is open and the base has a projection 4a which has a passage 4aa. The upper support member 5 is basically cylindrical in shape and is provided on its lower surface with a packing 6 for pressure contact with the plate 2 around the hole 2a. Peripheral welding or the like is used to attach the lower support member 4 and upper support member 5 together to thereby hold the specimen collection element 1. A syringe 7 is connected to the projection 4a of the lower support member 4 by a tube 8. A suction pump 9 is provided to pump air out via the passage 4aa. L denotes the body fluid being tested.

The specimen collection process will now be described. To collect test specimens from the body fluid L, the body fluid L is put into the upper support member 5. When the syringe 7 is used to create a negative pressure in the lower support member 4 via the tube 8, the liquid portion of the body fluid L passes from the upper support member 5 through the plastic film 3 and into the syringe 7, whereby the human cells are captured on the plastic film 3.

When there is no more body fluid L in the upper support member 5 or when the pores of the plastic film 3 become clogged with cells, preventing the passage of any more of the body fluid L, the lower support member 4 and upper support member 5 are opened and the plastic film 3 is removed and stained for microscopic examination. For simultaneous collection of multiple sets of specimens, the configuration of FIG. 14 can be used in which a plurality of specimen collection units, each consisting of a lower support member 4 and an upper support member 5, are arranged on a suction pump 9.

FIG. 15 is a side cross-sectional view of an another arrangement of a conventional apparatus for obtaining medical test specimens. Parts corresponding to those in the arrangements of FIGS. 12 to 14 have been given the same reference numerals, and further explanation thereof indicates omitted. In FIG. 15, reference numeral 10 is a cup into which the body fluid L represents placed, and 11 is a lid for the cup 10. The lid 11 is provided with a vent 11b and a hole 11a for the insertion of a tube 12 that reaches to the bottom of the cup 10.

Reference number 13 denotes a lower support member that has an open top and is provided in its base with a projection 13a with a passage 13aa that connects to the upper end of the tube 12. The upper inner surface of the lower support member 13 has a female thread. Reference number 14 denotes an upper support member which is provided on its outer surface with a male thread for engaging with the female thread of the lower support member 13, and a centrally located passage 14a that is connected to the syringe 7. By screwing the upper support member 14 into the lower support member 13, the specimen collection element 1 is held in an airtight state.

The specimen collection process will now be described. To collect test specimens from the body fluid L, the body fluid L is put into the cup 10, the lid 11 is closed and the tube 12 is inserted via the hole 11a into the cup 10 until the tube reaches the bottom of the cup 10. The syringe 7 connected to the passage 14a of the upper support member 14 is used to exert a negative pressure to draw the liquid portion of the body fluid L up through the tube 12 and lower support member 13 and into the syringe 7, whereby the cells in the fluid are captured on the plastic film 3.

When there is no more body fluid L in the cup 10 or when the pores of the plastic film 3 become clogged with cells, preventing the passage of any more of the body fluid L, the lower support member 13 and upper support member 14 are opened and the plastic film 3 is removed and stained for microscopic examination. For simultaneous collection of multiple sets of specimens, the configuration of FIG. 14 can be used in which a plurality of specimen collection assemblies each consisting of a cup 10, a lower support member 13 and an upper support member 14, are arranged on a suction pump 9.

In the case of the conventional specimen collection devices described above, when the lower support member 4 (or lower support member 13) and upper support member 5 (or upper support member 14) are opened after completion of the cell collection process, the remaining body fluid L sticks to the fingers and splashes around, which is unsanitary. In addition to this, when the syringe 7 (or suction pump 9) is detached from the tube 8 (or upper support member 14) to dispose of the body fluid L, the hands of the personnel holding the syringe are contaminated by the body fluid L. As the body fluid L may contain harmful bacteria, viruses, toxic substances and the like, it is necessary to sterilize the tube 8 and syringe 7 (suction pump 9) that are frequently touched by hands during specimen collection.

However, perfect sterilization of the personnel and equipment involved has a highly adverse affect on the efficiency of testing procedures, and sterilization that is less than complete can give rise to health risks. Moreover, microscopic examination can only take place after the plastic film 3 has been stained, put on a slide and covered with a cover glass, while if it is to be kept as a sample preparation it has to be sealed, but the specimen collection element 1 is not suitable for such procedures.

Also, it is important to apply the right amount of pressure to the lower support member 13. Too little pressure will result in insufficient filtration, while too much pressure will cause deformation of cells into the holes of the plastic film 3, giving rise to diagnostic errors, so the pressure has to be maintained at an appropriate level at all times. However, even slight changes in the volume of the suction pump 9 can cause major changes in the suction pressure applied to the non-compressible body fluid L, making it difficult to constantly maintain the required pressure, which fluctuates sharply between $0/cm^2$ and around $1/cm^2$, squeezing the cells into the holes of the plastic film 3 and making diagnosis difficult.

An object of the present invention is to provide a method and apparatus for collecting medical test specimens whereby cells can be collected without damaging them and the cleanliness of parts frequently touched by hand during the specimen collection process can be maintained, with none of the fluid being processed adhering to fingers or being splashed around.

SUMMARY OF THE INVENTION

In accordance with the present invention, the above object is attained by a method for collecting medical test specimens, comprising:

placing a sample fluid in a cup container having an outlet and pressurization means to increase the internal air pressure, disposing a specimen collection film so that it provides an airtight seal of the cup container outlet, and using the pressurization means to increase the air pressure in the cup to force the sample fluid out through the outlet and capture specimens in the sample fluid on the film.

The above object is also attained by a specimen collection apparatus, comprising:

a specimen collection element constituted by a thin, stiff plate that is provided with a hole at one end and a film for capturing specimens affixed to one surface of the plate so that the film covers the hole, a lower cup open at the top that is provided with a hole in its peripheral wall for inserting the specimen collection element and has a central hollow holder, an upper cup the lower portion of which can be detachably engaged with the top of the lower cup, is provided with an outlet in its base at a position corresponding to the position of the holder in the lower cup and engages with the lower cup to form an airtight state when the specimen collection element is inserted, a liquid permeable spacer that is mounted on the holder of the lower cup in contact with the film of the inserted specimen collection element, and means for increasing the air pressure in the upper cup.

Thus, in accordance with the method for collecting medical test specimens of this invention the specimen capture film is arranged to form an airtight seal over the outlet of the container cup, and by increasing the pressure in the cup, the sample fluid is forced through the outlet to thereby capture specimens on the film. Therefore, the compressed air has a cushioning effect that enables specimen cells to be captured without deforming the cells.

Also, with the apparatus for collecting medical test specimens according to this invention, the upper and lower cups engage to form an airtight fit, which is hygienic as it prevents external leakage of the sample fluid.

Further features of the invention, its nature and various advantages will become more apparent from the accompanying drawings and following detailed description of the invention.

DESCRIPTION OF THE PREFERRED EMBODIMENTS

Figure 1:
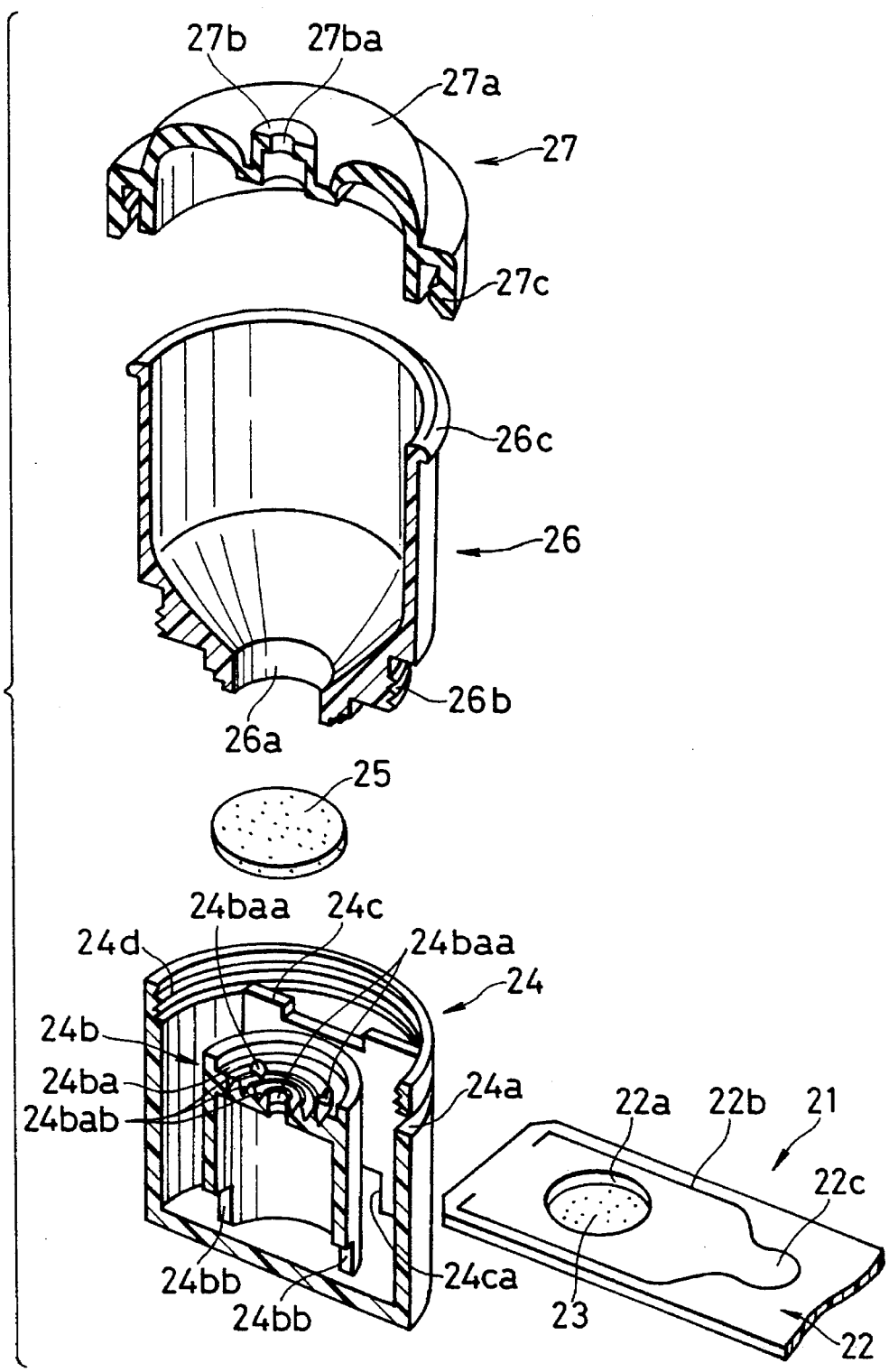
FIG. 1 is a cross-sectional disassembled perspective view of an embodiment of a specimen collection apparatus according to this invention.

An embodiment of the specimen collection apparatus of the present invention will now be described with reference to FIGS. 1 to 4. In the drawings, reference numeral 24 denotes a plastic lower cup. Provided in the wall of the lower cup 24 is an elongated hole 24a via which a specimen collection element 21 is inserted, and provided in the base is a hollow spacer holder 24b the upper portion of which has a spacer rest 24ba for a spacer 25 that contacts a film 23 on the specimen collection element 21 inserted via the hole 24a. A guide member 24c is provided at each side of the spacer holder 24b for guiding the specimen collection element 21 inserted into the hole 24a. The upper inside surface of the lower cup 24 has a female thread 24d.

A water absorbing agent 28 is contained in the bottom part of the cup 24. The water absorbing agent may be a known water absorbing resin such as acrylamide copolymer hydrolysate, self-bridge type neutralized polyacrylate or a modified bridged polyvinyl alcohol powder or the powder may be inserted in a water-permeable bag.

Figure 3:
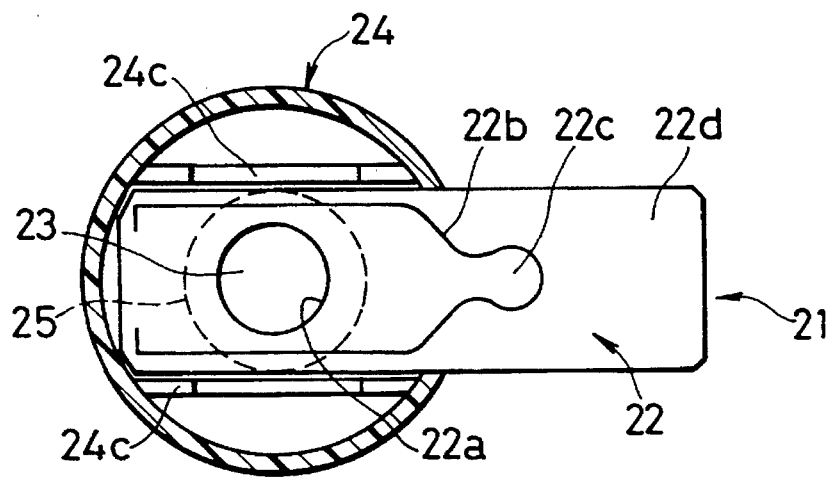
FIG. 3 is a cross-sectional view taken along line III—III of FIG. 2.
Figure 4:
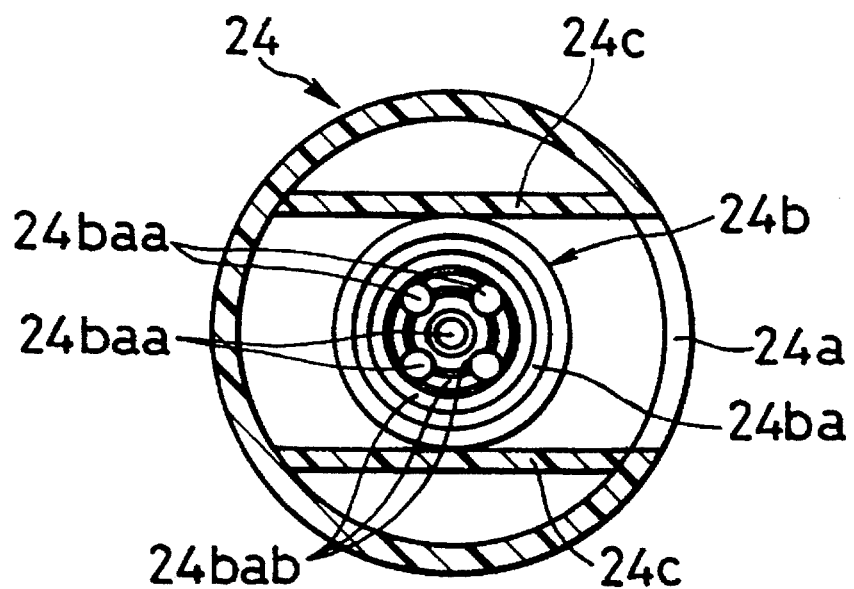
FIG. 4 is a cross-sectional view taken along line IV—IV of FIG. 2.
Figure 5:
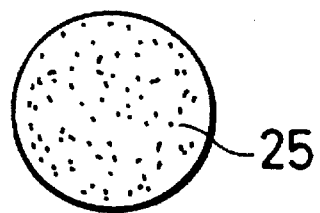
FIG. 5 is a plan view of the spacer used in the specimen collection apparatus of FIG. 1.
Figure 6:
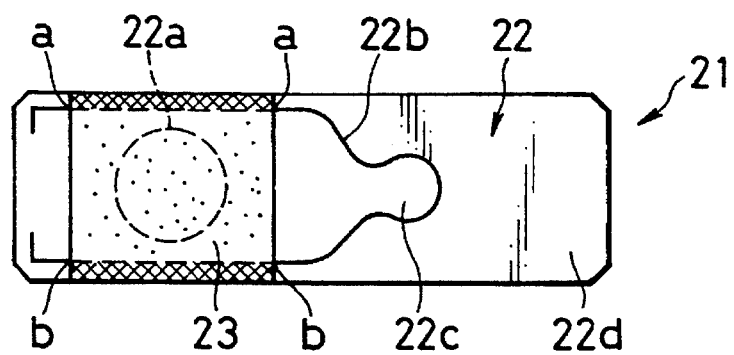
FIG. 6 is a rear view of the specimen collection element of the specimen collection apparatus of FIG. 1.
Figure 7:
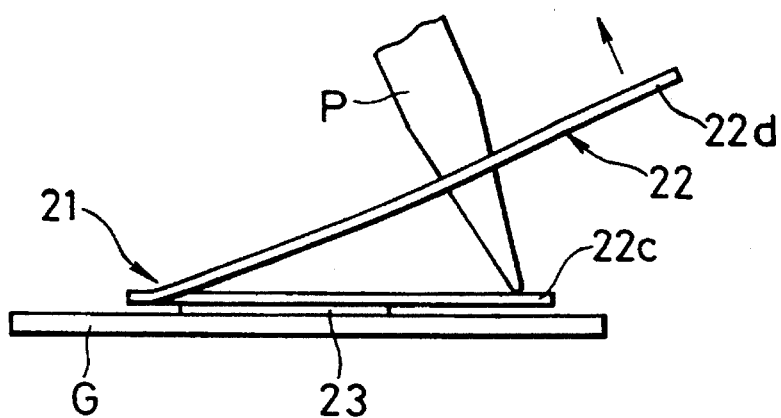
FIG. 7 shows the film from the specimen collection element of FIG. 6 attached to a slide.

As shown by FIGS. 3 and 6, the specimen collection element 21, which is roughly the shape of a microscope slide, consists of a stiffly flexible plate 22 with a round hole 22a at one end and a cut-in 22b that is not complete at one end and at the other end is in the shape of a projection 22c, and a grip portion 22d, and a film 23 bonded or otherwise attached at each end to the plate 22 on the outside of the cut-in 22b so as to cover the hole 22a.

The film 23 that forms the filter for the sample fluid is extremely thin, being about 10 μm thick, and is uniformly and densely provided over its entire surface with holes about 5 μm in diameter. The film 23 may be formed of polypropylene, polycarbonate, polyester or other such plastic material, or it may be of stainless steel, metal foil or paper or the like.

The base of the spacer rest 24ba is provided with, a plurality of holes 24baa that communicate with the interior part of the spacer holder 24b, and concentric grooves 24bab that are in contact with the holes 24baa. The lower part of the spacer holder 24b and guide members 24c are also provided with holes 24bb and holes 24ca to join the segmented spaces. A porous, water-permeable spacer 25 fits on top of the spacer rest 24ba, and is larger than the hole 22a.

Reference numeral 26 denotes an upper cup 26 the bottom of which is provided with an outlet 26a that is substantially the same shape and size as the hole 22a. The lower outer surface of the upper cup 26 has a male thread 26b for engaging with the female thread 24d of the lower cup 24, and the upper outer surface of the upper cup 26 is provided with an engaging portion 26c that widens downwardly.

Reference numeral 27 denotes a cap formed of a flexible material and constitutes the pressurization means. The cap 27 has a central diaphragm 27a the center of which has an upward bulge, a thick boss 27b with a vent 27ba. Provided around the diaphragm 27a is a detachable, undercut engaging portion 27c which engages with the engaging portion 26c of the upper cup 26 to form an airtight fit.

Figure 2:
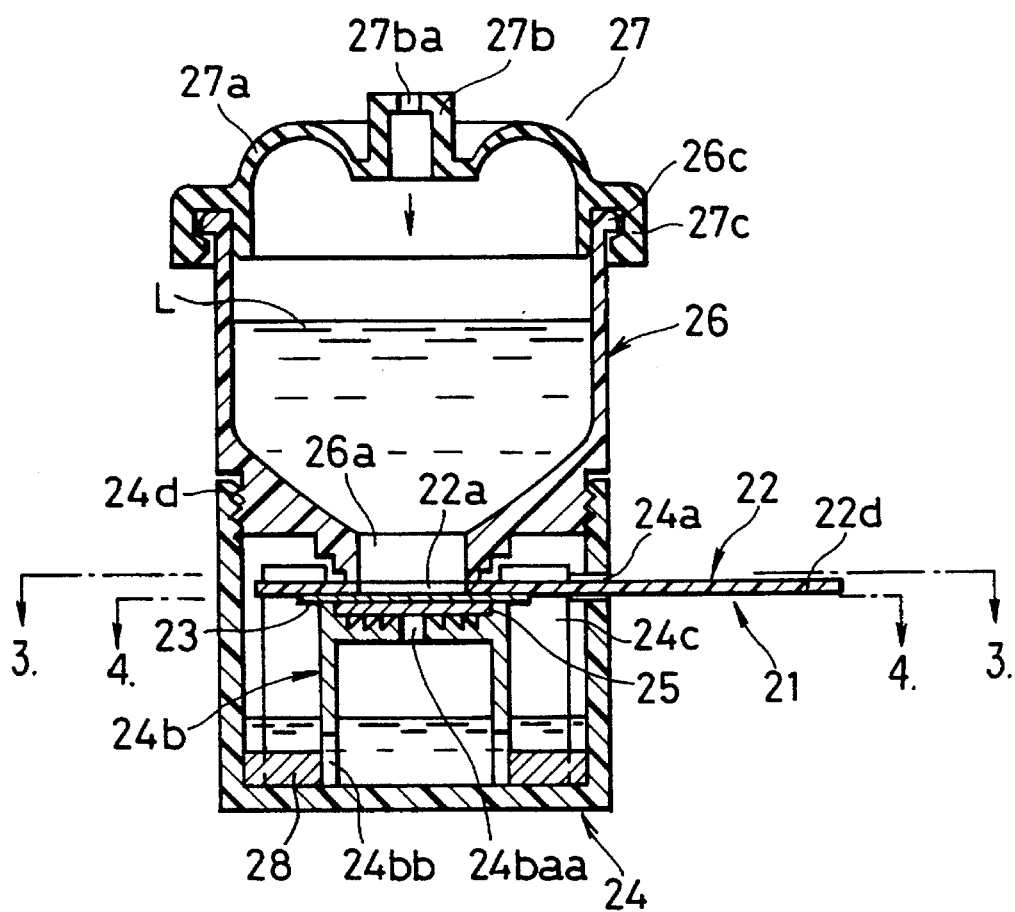
FIG. 2 is a cross-sectional view of the assembled specimen collection apparatus of FIG. 1.

Assembly and specimen collection will now be described. First, the spacer 25 is placed on the spacer rest 24ba the male thread 26b is screwed slightly into the female thread 24d, and the specimen collection element 21 is inserted via the hole 24a so that, as shown in FIG. 2, the film 23 is on the lower surface, and the hole 22a is concentric with the outlet 26a. The specimen collection element 21 inserted via the hole 24a is guided by the guide members 24c.

Next, the male thread 26b is screwed tightly into the female thread 24d, thereby clamping the plate 22, film 23, spacer 25 and spacer holder 24b together. The body fluid L is then put into the upper cup 26 and the upper cup 26 is closed by the cap 27, forming an airtight seal between the engaging portion 26c and engaging portion 27c. When the cap 27 is thus in position, covering the vent 27ba with a finger and pushing the boss 27b to resiliently deform the diaphragm 27a downwards compresses the air inside, exerting pressure on the body fluid L that causes the liquid component of the body fluid L to pass through the holes of the film 23 and enter the lower cup 24 via the grooves 24bab and holes 24baa.

The presence of the spacer 25 means that at this time there is no direct contact between the film 23 and spacer holder 24b, which improves the efficiency of the filtration and prevents specimens being deformed. As the liquid collecting in the lower cup 24 is absorbed by the water absorbing agent 28, which is hygienic as it ensures that there is no spillage outside the apparatus.

If one push on the boss 27b is not enough to filter all the fluid, the finger of the operator conducting the testing is taken off the boss 27b to allow air to enter through the vent 27ba, whereby the resilience of the cap 27 causes it to revert to its initial shape. When the boss 27b has thus been pressed two or three times to more or less complete the filtration process, the male thread 26b and female thread 24d are loosened to slightly separate the spacer holder 24b and the upper cup 26, and the grip portion 22d is used to extract the specimen collection element 21 without opening the lower cup 24 and upper cup 26.

Figure 8:
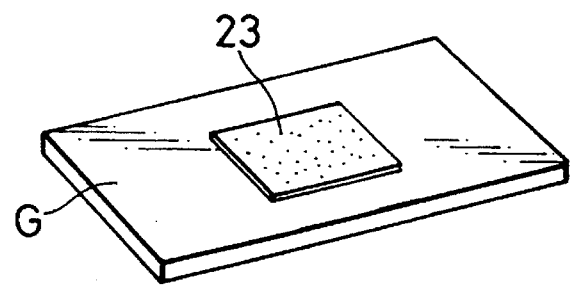
FIG. 8 is a perspective view of the film attached to the slide.

The specimen collection element 21 thus extracted is subjected to the staining process and is then positioned on a slide G with the film 23 facing downward, and a pair of forceps P or the other such means is used to press the projection 22c part of the cut-in 22b down onto the slide G while lifting up the grip portion 22d, separating the film 23 at the two points a-a and b-b (FIG. 6) corresponding to the lines of the cut-in 22b and thereby leaving just the film 23 on the slide G, as shown by FIG. 8. A cover glass can then be applied for observation under the microscope, or it can be sealed to form a sample preparation.

The arrangement of this embodiment is hygienic, as the body fluid L is absorbed by the water absorbing agent 28 and therefore even if the lower cup 24 and upper cup 26 are loosened to remove the specimen collection element 21, the body fluid L does not get onto to fingers or get splashed around.

The cap 27 is frequently touched by the operator during the specimen collection procedure but does not contact the body fluid L, so that the cleanliness of the cap 27 can be maintained and repeated use is possible without any special sterilization procedures being required. The arrangement is still hygienic even if no water absorbing agent 28 is used, as there will be no spillage from the lower cup 24 as long as the apparatus does not fall over or the amount of the body fluid L put into the upper cup 26 does not exceed the capacity of the lower cup 24.

In the above arrangement in which cells are filtered out by increasing the air pressure in the upper cup 26, the compressed air has a cushioning effect that provides good pressure stability, so that by maintaining a constant ratio between the displacement produced by the deformation of the diaphragm 27a and the internal volume of the upper cup 26, that is, the compression ratio, the pressure will remain constant whether the boss 27b is pressed slowly or quickly. If the compression ratio is 1:5, the pressure will be 0.2 kg/cm$^2$.

Figure 9:
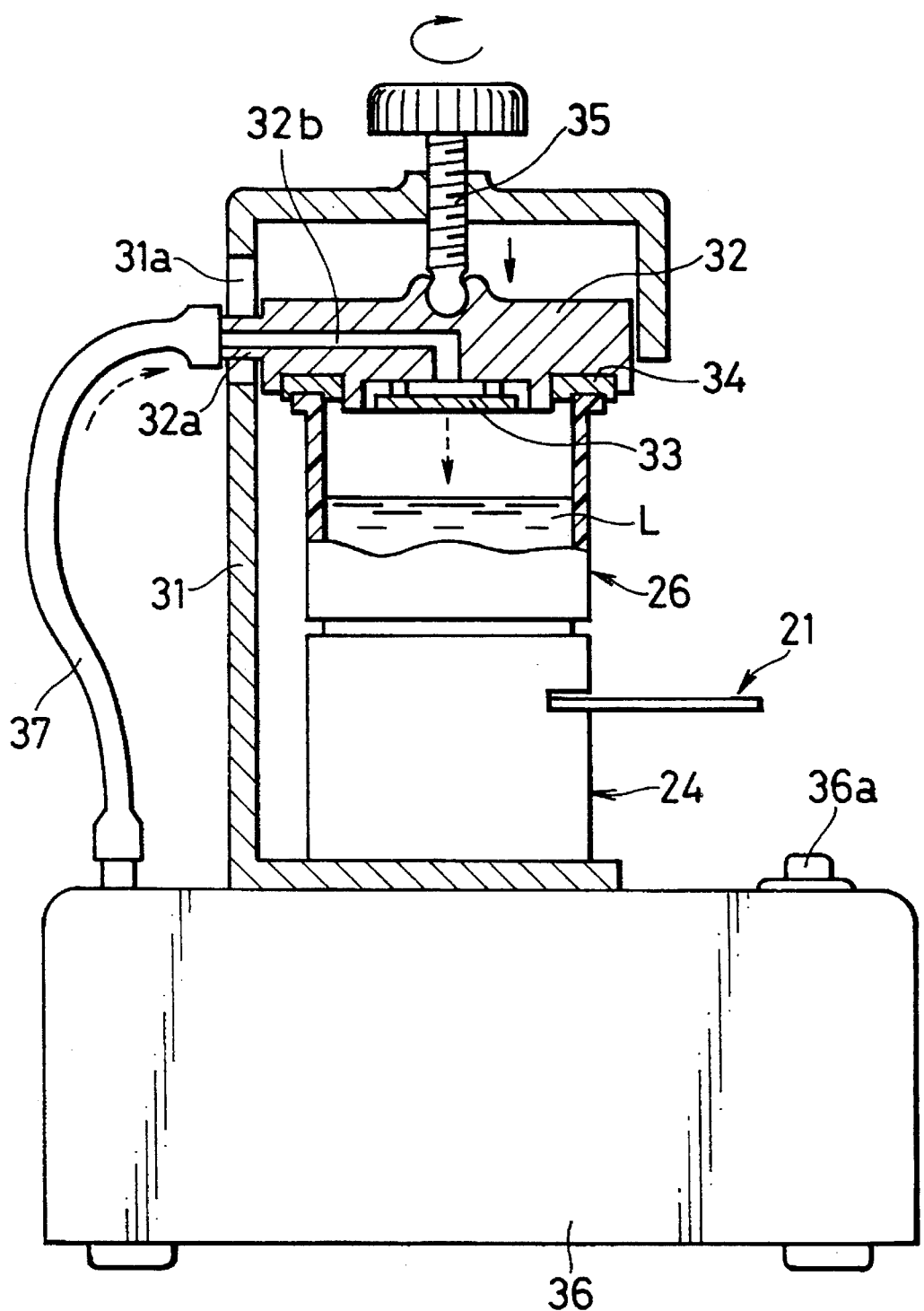
FIG. 9 is a cross-sectional side view of another embodiment of the specimen collection apparatus of the invention.

As such, no matter who is conducting the specimen collection operation, as long as normal conditions are maintained the pressure will not become high enough to deform or destroy specimen cells. Also, as the film 23 is attached to the plate 22 which is substantially the same shape and size as the slide G, it can be used as-is in standard staining systems, and after the staining just the film 23 can be attached to the slide G, making it possible to readily use it as a sample preparation by adding a cover glass and sealing FIG. 9 is a cross-sectional side view of another embodiment of the specimen collection apparatus of the invention, which can be used for high volume filtration. Parts corresponding to those in the arrangements of FIGS. 1 to 8 have been given the same reference numerals, and further explanation thereof is omitted.

In FIG. 9, reference numeral 31 denotes a rigid frame. The lower part of the front plate of the frame 31 is open, and the upper part of the back plate is provided with an elongated hole 31a. Inside the frame 31 is a pressure top 32, which is provided with a baffle plate 33 affixed to the center of the lower surface of the pressure top 32, packing 34 which abuts against the top edge of the upper cup 26, a projection 32a that projects into the elongated hole 31a, and a vent 32b that communicates with the upper surface (back) of the baffle plate 33.

The lower end of a screw 35 located in the top plate of the frame 31 is rotatably engaged with pressure top 32. Reference number 36 is an air compression pump. When the air compression pump 36 is started by pressing a switch 36a, the air compression pump 36 pumps out air at a prescribed pressure. The projection 32a of the pressure top 32 is connected to the air compression pump 36 by a hose 37.

Assembly and specimen collection will now be described. An assembly unit consisting of the specimen collection element 21 held by the lower cup 24 and upper cup 26 is placed in the frame 31, and the screw 35 is rotated to lower the pressure top 32 and bring the packing 34 into airtight contact with the upper cup 26. When the switch 36a is pressed to start the air compression pump 36, the pump 36 supplies the pressure top 32 with air compressed at a pressure of 0.2 kg/cm², for example, to thereby enable specimens to be obtained as described above.

When specimen filtration has been completed, the switch 36a is pressed to stop the pump 36 and the screw 35 is slackened off, raising the pressure top 32, and the lower cup 24, upper cup 26 and specimen collection element 21 assembly is removed from the frame 31, to be replaced by the next sample to be processed. The baffle plate 33 reduces the air flow velocity and, by preventing the compressed air from blowing directly onto the film 23, prevents the film 23 from being dried out.

The delivery pressure of the air compression pump 36 can be set to a value between 1 kg/cm² and 0.4 kg/cm² that is appropriate for the specimen cells. High volume specimen collection can be implemented by an arrangement consisting of an array of frames 31 each containing an assembly unit comprised of a specimen collection element 21, lower cup 24 and upper cup 26, and using an air compression pump 36 to deliver compressed air to each pressure top 32. Thus, the above embodiment can provide the same effect as that of the preceding embodiment. Moreover, the amount of pressure fluctuation caused by slight wear to the parts is far less than is the case with a pump used for pumping non-compressible liquids.

Figure 10:
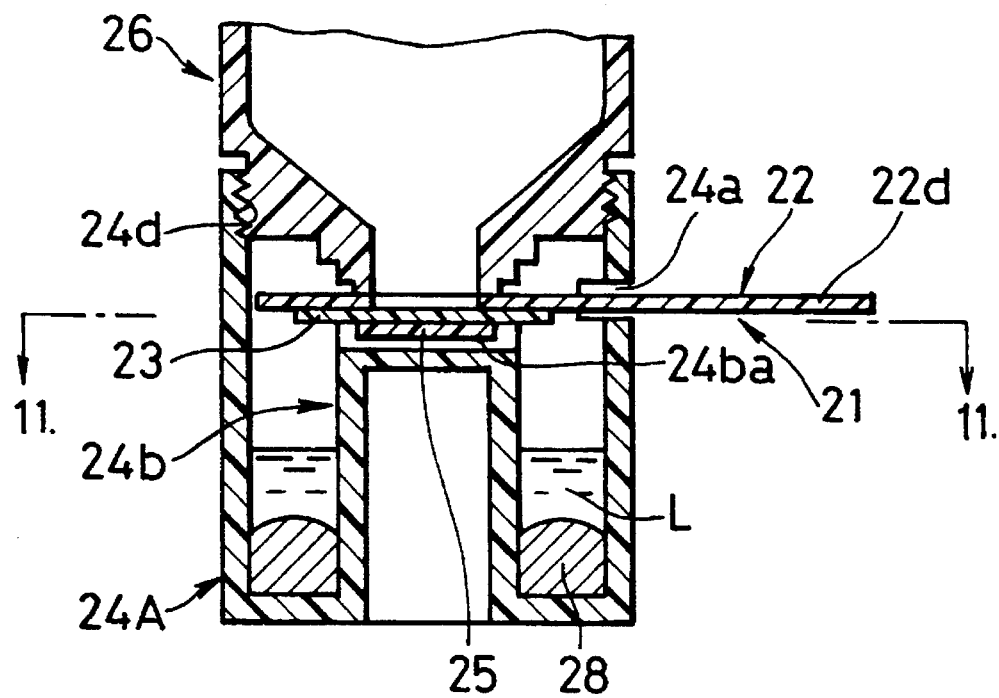
FIG. 10 is a cross-sectional side view of yet another embodiment of the specimen collection apparatus of the invention.
Figure 11:
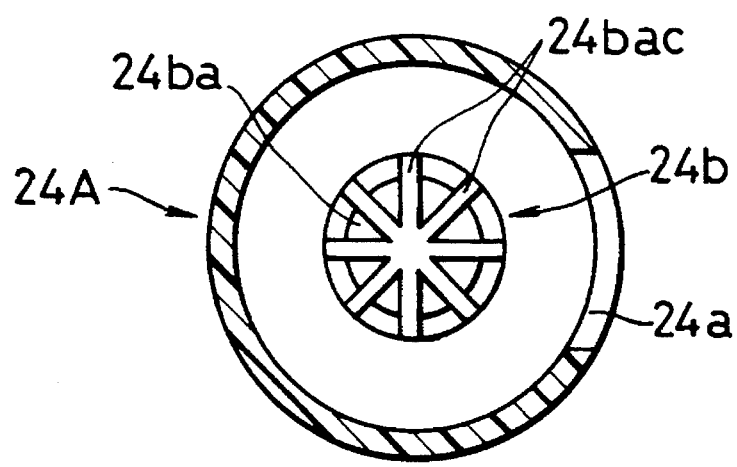
FIG. 11 is a cross-sectional view taken along line XI—XI of FIG. 10.
Figure 12:
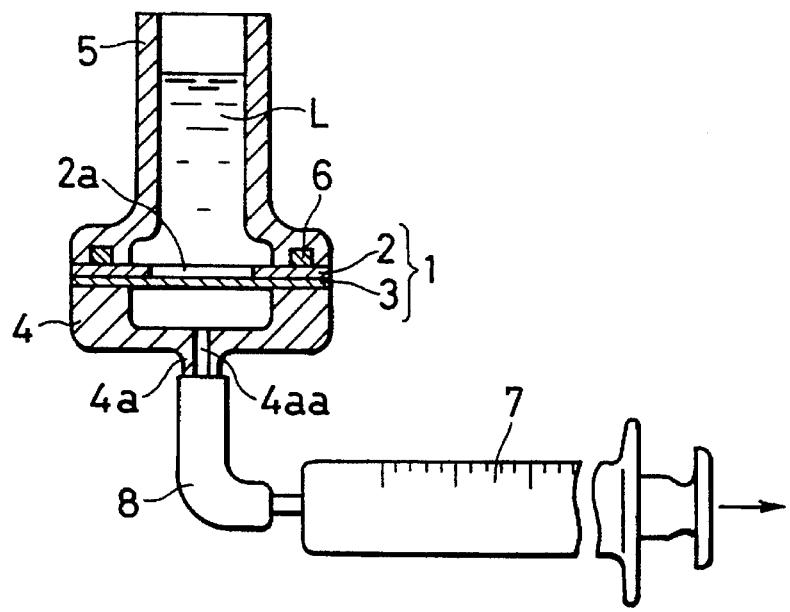
FIG. 12 is a partial cross-sectional view of a conventional specimen collection apparatus.
Figure 13:
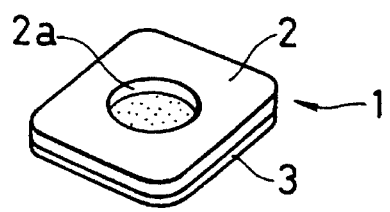
FIG. 13 is a perspective view of a conventional specimen collection element.
Figure 14:
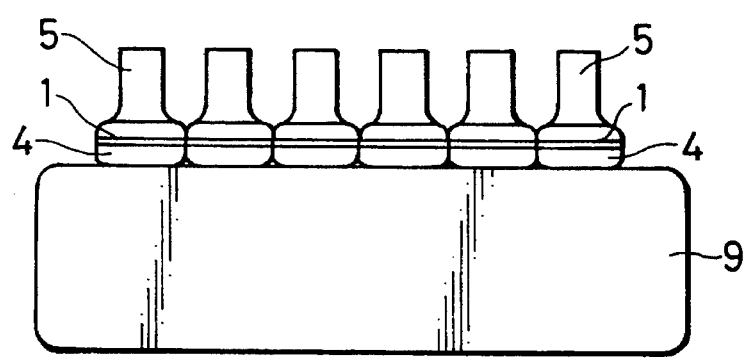
FIG. 14 shows a conventional array of multiple specimen collection apparatuses arranged on a suction device.
Figure 15:
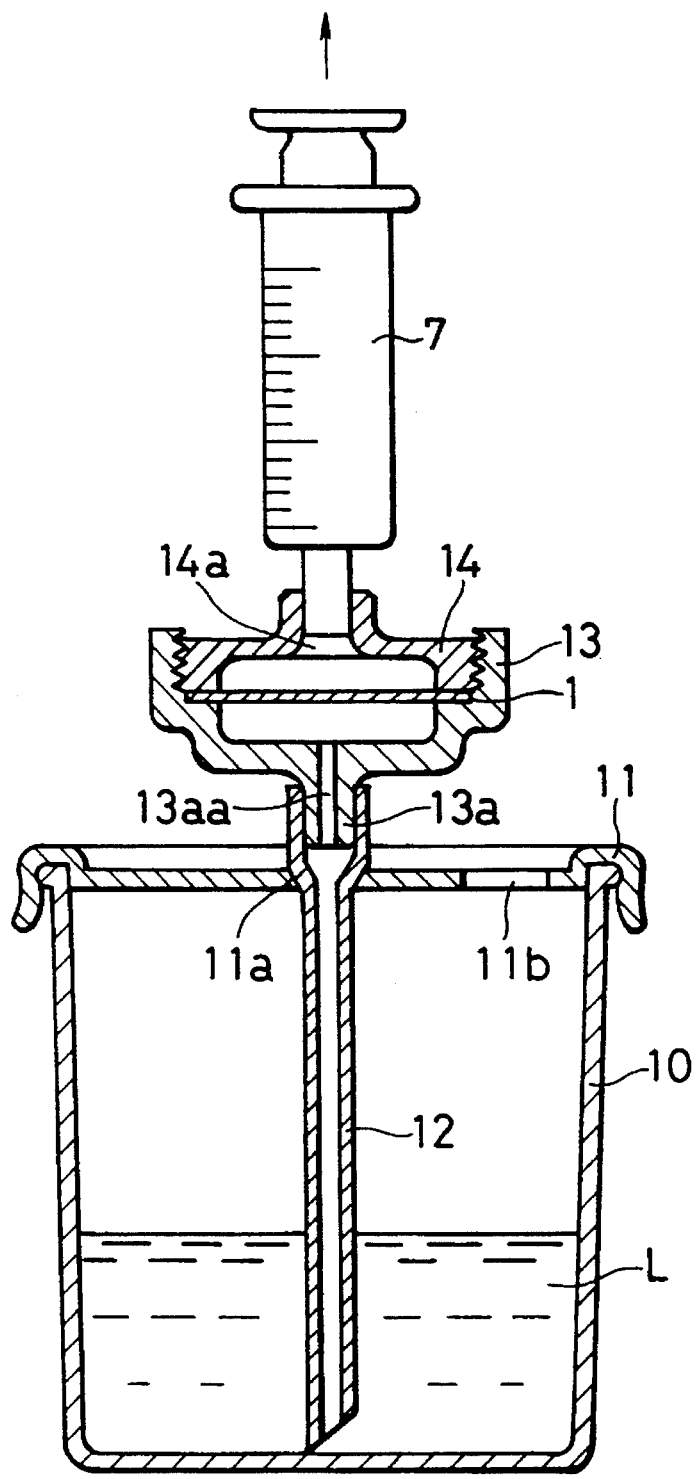
FIG. 15 is a partial cross-sectional side view of another example of a conventional specimen collection apparatus.

FIG. 10 is a cross-sectional side view of the main parts of another embodiment of the specimen collection apparatus of the invention, and FIG. 11 is a cross-sectional view through line XI—XI of FIG. 10, with the spacer removed. Parts corresponding to those in the arrangements of FIGS. 1 to 9 have been given the same reference numerals, and further explanation thereof is omitted.

In FIGS. 10 and 11, reference numeral 24A denotes a lower cup of plastic. Provided in the wall of the lower cup 24A is an elongated hole 24a via which a specimen collection element 21 is inserted, and provided in the base is a hollow spacer holder 24b the upper portion of which has a spacer rest 24ba for a spacer 25 that contacts a film 23 on the specimen collection element 21 inserted via the hole 24a. The upper inside surface of the lower cup 24 has a female thread 24d. The base of the spacer rest 24ba is provided with a plurality of radial grooves 24bac that support the film 23 and communicate with the lower cup 24A.

Assembly and specimen collection are the same as in the other embodiments, so further explanation thereof is omitted. This configuration enables the lower cup 24A to be formed in one piece, facilitating fabrication.

The above embodiments have been described with reference to the use of a male thread 26b mating with a female thread 24d to enable the specimen collection element 21 to be maintained in an airtight state by the lower cup 24 (24A) and upper cup 26. However, this objective may also be accomplished by other means, such as a bayonet fitting or lever clamp, for example. Similarly, while the above description has been made with reference to the use of a screw 35 to effect an airtight fit between the pressure top 32 and the upper cup 26, the same effect may be attained using other means, such as for example a bayonet fitting or lever clamp, Also, the embodiment illustrated by FIGS. 10 and 11 may be provided with a guide member 24c on each side of the spacer holder 24b for guiding the specimen collection element 21 inserted via the hole 24a. The invention is not limited to diagnostic applications, being also applicable to treatment and any field in which fluid analysis is used.

As has been described in the foregoing, in accordance with the specimen collection method of this invention, a sample fluid contained in a cup is caused to flow from the cup outlet by using a pressurization means to increase the air pressure in the cup, whereby specimens are captured on a film attached across the outlet in an airtight fit, and the cushioning effect of the compressed air provides good pressure stability, so that there is none of the type of deformation and destruction of specimens that can be caused by excess pressure.

In accordance also with the specimen collection apparatus according to the invention, the specimen collection element is held in an airtight condition by an upper cup and a lower cup, and a pressurization means is used to increase the air pressure in the upper cup, forcing the liquid portion of the sample in the upper cup to pass through the film filter and spacer and into the lower cup, in the course of which the specimens concerned are retained on the film. Again, therefore, the cushioning effect of the compressed air provides good pressure stability, preventing any deformation and destruction of specimens that might otherwise arise from the application of excessive pressure.

Furthermore, the 1 arrangement is clean and hygienic, as it ensures that when the specimen collection element is removed from the airtight state in which it is maintained by the lower and upper cups, sample fluid does not get onto the fingers or get splashed around. In addition, the pressurization means that is frequently touched by operators' hands during the specimen collection procedure does not come into contact with the sample fluid, and can therefore be readily maintained in its clean state through repeated use cycles without needing to be specially sterilized, making it possible to conduct specimen collection efficiently and hygienically. A further advantage is that as the specimen plate is about the same shape and size as a normal microscope slide, it can be used with standard staining systems.

What is claimed is:

1. A specimen collection apparatus, comprising:
    a specimen collection element which includes a plate provided with a hole at one end and a film capturing specimens affixed to one surface of the plate so that the film covers the hole, a lower cup closed at the bottom portion thereof, said lower cup having a hole in a peripheral wall thereof for inserting the specimen collection element and which has a central hollow holder, an upper cup the lower portion of which is detachably engaged with a top portion of the lower cup, said upper cup having an open top and being provided with an outlet in a base portion thereof at a position corresponding to the position of the holder in the lower cup and which engages with the lower cup to form an airtight state when the specimen collection element is inserted therein, a liquid permeable spacer mounted on the holder of the lower cup in contact with the film of the inserted specimen collection element, and a compression mechanism positioned on said open top of said upper cup, said compression mechanism increasing the air pressure in the upper cup and including one of a pressurization cup and a pressurization top and an air pressure source which increases the air pressure in the upper cup.

2. The apparatus according to claim 1, wherein the bottom of the lower cup is provided with a water absorber.

3. The apparatus according to claim 1 wherein the film is a plastic film provided over its entire surface with holes about 5 μm in diameter.

4. The apparatus according to claim 1, wherein the upper cup is formed of a flexible material.

\* \* \* \* \*